United States Patent
Schröder

(10) Patent No.: US 7,731,982 B2
(45) Date of Patent: Jun. 8, 2010

(54) O/W EMULSIFIER, O/W EMULSION AND APPLICATIONS THEREOF

(75) Inventor: Bernd Schröder, Holzminden (DE)

(73) Assignee: Symrise GmbH & Co. KG, Holzminden, DE (US)

( * ) Notice: Subject to any disclaimer, the term of this patent is extended or adjusted under 35 U.S.C. 154(b) by 1205 days.

(21) Appl. No.: 10/561,224

(22) PCT Filed: May 28, 2004

(86) PCT No.: PCT/EP2004/050961

§ 371 (c)(1),
(2), (4) Date: Dec. 19, 2005

(87) PCT Pub. No.: WO2004/112731

PCT Pub. Date: Dec. 29, 2004

(65) Prior Publication Data

US 2006/0165738 A1    Jul. 27, 2006

(30) Foreign Application Priority Data

Jun. 26, 2003   (DE) .............................. 103 28 686
Jul. 14, 2003   (DE) .............................. 103 31 760

(51) Int. Cl.
  *A61K 8/00*   (2006.01)

(52) U.S. Cl. ..................................................... 424/401
(58) Field of Classification Search ..................... None
  See application file for complete search history.

(56) References Cited

FOREIGN PATENT DOCUMENTS

| JP | 2003061572 |   | 4/2003 |
| JP | 2003061572 | * | 3/2009 |
| WO | WO 99/37282 |   | 7/1999 |

OTHER PUBLICATIONS

Prosperio G et al., Neuere essbare O/W-Emulgator-Mischungen Riechstoffe Aromen Kosmetica (RAK), Fachverlag v. Frankenstein. Eschershausen.

* cited by examiner

*Primary Examiner*—Robert A Wax
*Assistant Examiner*—Melissa S Mercier
(74) *Attorney, Agent, or Firm*—Roylance, Abrams, Berdo & Goodman, L.L.P.

(57) ABSTRACT

The invention concerns an O/W emulsifier, an O/W emulsion prepared therefrom and the uses thereof. According to the invention the O/W emulsifier contains
  (a) 70 to 90 wt. % of glyceryl oleate citrate and
  (b) 10 to 30 wt. % of a viscosity modifier having a viscosity in the range from 1 to 10,000 mPas.

21 Claims, No Drawings

O/W EMULSIFIER, O/W EMULSION AND APPLICATIONS THEREOF

FIELD OF THE INVENTION

The invention concerns an O/W emulsifier, an O/W emulsion prepared therefrom and the uses thereof.

BACKGROUND OF THE TECHNOLOGY

As the largest organ in the human body, the human skin performs many vital functions. With an average surface area of approximately 2 $m^2$ in adults, it has a prominent role as a protective and sensory organ. It is the job of this organ to communicate and repel mechanical, thermal, actinic, chemical and biological stimuli. It also has an important role as a regulatory and target organ in the human metabolism.

Cosmetic skin care is primarily concerned with reinforcing or restoring the natural function of the skin as a barrier against environmental influences (e.g. dirt, chemicals, microorganisms) and against the loss of bodily substances (e.g. water, natural fats, electrolytes) and to support the natural regeneration ability of its stratum corneum if it becomes damaged. If the barrier properties of the skin are disrupted, this can lead to greater resorption of toxic or allergenic substances or to attack by microorganisms, resulting in toxic or allergenic skin reactions. A further objective of skin care is to compensate for the loss of fat and water in the skin caused by daily washing. This is especially important if the natural regeneration ability is not adequate. Skin care products should also protect against environmental influences, particularly sun and wind, and delay skin ageing.

Medical topical compositions generally contain one or more drug products in an active concentration. In the interests of simplicity, in order to obtain a clear distinction between cosmetic and medical usage and corresponding products, reference is made to the legal provisions of the Federal Republic of Germany (e.g. the German Cosmetics Ordinance, Food Act and Drugs Act).

Emulsions are understood to be heterogeneous systems comprising two liquids which are immiscible or have only limited miscibility with each other and which are conventionally known as phases. In an emulsion, one of the two liquids is dispersed in the other liquid in the form of extremely fine droplets. If the two liquids are water and oil and oil droplets are finely dispersed in water, it is an oil-in-water emulsion (O/W emulsion, e.g. milk). The basic character of an O/W emulsion is shaped by the water. In a water-in-oil emulsion (W/O emulsion, e.g. butter), the principle is reversed and the basic character is determined by the oil. The person skilled in the art is naturally aware of many possibilities for formulating stable O/W preparations for cosmetic or dermatological use, for example in the form of creams and ointments which are spreadable in the range from room temperature to skin temperature, or as lotions and milks, which are more flowable in this temperature range. These systems generally contain emulsifiers.

Emulsifiers are auxiliary substances for the preparation and stabilisation of emulsions which are generally in the form of oily to waxy, but also powdered, substances. In order to stabilise emulsions over an extended period, emulsifiers are needed which suppress or delay the separation of the two phases, e.g. oil and water, to the thermodynamically stable final state until the emulsion has fulfilled its purpose.

Emulsifiers lower the interfacial tension between the two phases and as well as reducing interfacial activity also stabilise the emulsion that is formed. Emulsifiers stabilise the emulsion that is formed by means of interfacial films and by forming steric or electrical barriers, preventing the flowing together (coalescence) of the emulsified particles. Both the elasticity and the viscosity of the interfacial films are important factors in emulsion stabilisation and are strongly influenced by the emulsifier. Stabilising an emulsion which has already been formed is the most important property of emulsifiers, and more important than facilitating the primary distribution of the phases, since an adequate number of mechanical aids are available for this purpose. The most important requirements of emulsifiers are as follows:

a) The emulsifier must concentrate at the boundary layer between the phases. To this end it must have interface-active or surface-active properties, in other words reduce the interfacial tension of the immiscible phases.

b) The emulsifier must also either charge the particles so that they repel one another or form a stable, often highly viscous or even solid protective layer around the particles.

These properties are sufficient in themselves for many applications. For the preparation of emulsions which are stable over a particularly long period, however, the creaming or sedimentation of the dispersed particles must be prevented and their tendency to coalesce still further reduced. This is achieved by increasing the viscosity of the outer phase and/or forming protective viscous structures, e.g. liquid crystalline or gel phases. In this case, in addition to the emulsifier itself, the emulsifier system must also contain an additional component known as a co-emulsifier, stabiliser or also, depending on the active mechanism, as a consistency modifier or protective colloid.

In order for compounds to be effective as an emulsifier, they must exhibit a particular molecular structure. The structural feature of such compounds is their amphiphilic molecular structure. The molecule in such a compound has at least one group with affinity to high-polarity substances (polar group) and at least one group with affinity to non-polar substances (apolar group). The polar group is a functional group whose electron distribution gives the molecule a considerable dipole moment. This group determines the affinity to polar liquids, particularly the affinity to water, and the hydrophilic nature of the compound. For that reason the polar function is also called the hydrophilic group.

The apolar group, on the other hand, is the part of the molecule whose electron distribution makes no significant contribution to the dipole moment. The apolar group determines the affinity to apolar liquids, particularly low-polarity organic solvents, for which reason this function is also called the lipophilic group. The combined presence of hydrophilic and lipophilic groups in the molecule allows emulsifiers to interact with both hydrophilic and lipophilic phases. This leads to an orientation at the interface which is the precondition for the interfacial activity of such compounds.

A decisive feature for the characterisation of emulsifiers is the ratio of hydrophilic to lipophilic constituents in the molecule, expressed as the hydrophilic-lipophilic balance (HLB system), for the determination of which there are many experimental and theoretical mathematical methods, all of them based on determining the ratio of hydrophilic to lipophilic groups in the molecule component. Emulsifiers with a high HLB value produce O/W emulsions, those with a low HLB value preferentially form W/O emulsions.

However, only a few O/W emulsifiers are known from the prior art which form such low-viscosity O/W emulsions that these would be sprayable, for example. Most of them contain polyethylene glycols. Furthermore, low-viscosity O/W emulsions of the prior art commonly have the disadvantage of being unstable, limited to a narrow range of applications or to a restricted choice of constituents. For that reason there are currently no low-viscosity, cold-processable O/W emulsions on the market in which for example highly polar oils—such as the plant oils otherwise commonly used in commercial products—are adequately stabilised. According to the prior art, O/W emulsions having a low viscosity and displaying a storage stability such as is required for marketable products can be formulated only with great difficulty. The choice of such formulations is accordingly extremely limited. Nevertheless, such formulations could offer the consumer previously unknown cosmetic benefits.

A low-viscosity cosmetic or dermatological O/W emulsion is known from EP 1 049 452 which contains one or more partially neutralised esters of monoglycerides and/or diglycerides of saturated fatty acids with citric acid and one or more fatty alcohols chosen from the group comprising branched and unbranched alkyl alcohols having 12 to 40 carbon atoms.

US 2003/0012801 discloses a special emulsion which contains one or more partially neutralised esters of monoglycerides and/or diglycerides of saturated fatty acids with citric acid, cyclodextrins and retinoids.

A hair care agent is known from WO 99/62468 which in addition to a special pentaerythritol ester oil contains a second oil component. Citric acid ester oils having a very generalised formula with unsaturated alkyl radicals having between 1 and 30 carbon atoms are claimed inter alia as an example for the second oil component. Specific compounds from this class of substances are not listed.

SUMMARY OF THE INVENTION

The object underlying the present invention is in particular to provide an O/W emulsifier which overcomes the disadvantages of the prior art.

This object is achieved by the O/W emulsifier with the features cited in claim 1 and the uses associated therewith.

According to the invention the O/W emulsifier contains
(a) 70 to 90 wt. % of glyceryl oleate citrate and
(b) 10 to 30 wt. % of a viscosity modifier having a viscosity in the range from 1 to 10,000 mPas.

The O/W emulsifier according to the invention is principally characterised by the following:

Ability to be prepared from O/W emulsions by the hot/hot, hot/cold and in particular the cold/cold process
Formation of thermostable emulsions even when used in low concentrations of e.g. less than 2%,
Its versatile suitability both for higher-viscosity creams, medium-viscosity milks and lotions and for low-viscosity, sprayable lotions
An improved dispersion of solids in emulsion systems in comparison to known O/W emulsifiers,
Greater dispersibility of incorporated solids in comparison to known O/W emulsifiers,
A largely pH-independent behaviour in the recipes formulated therewith,
Its ability to be used in formulations with both polar and non-polar oils,
Its compatibility with hydrogel formers and hydrocolloids,
The absence of polyethylene glycols,
Its ability to be combined with co-emulsifiers and consistency-modifying components and
Its ability to be combined with UV-A and UV-B filters to improve the water adhesion of sunscreen products.

O/W emulsions prepared with the emulsifier are principally characterised by the following:

Production with low energy costs: the water phase or even the water and oil phase (with an appropriate choice of the other components) are cold-processable,
A good viscosity stability,
A high pH stability
A good temperature stability,
Very fine and homogeneous emulsion structures with a glossy surface,
Straight-forward incorporation of polar and non-polar oils, wherein incorporation of the O/W emulsifier can take place via the water phase or oil phase as preferred, and
Commercial and logistical advantages in terms of the procurement and storage of a single O/W emulsifier for lotions and creams.

DETAILED DESCRIPTION

The glyceryl oleate citrate is preferably an ester of monooleic and/or dioleic acid glycerides with citric acid, wherein the ester is obtainable in particular by esterification of citric acid with monooleic acid glyceride in a molar ratio of 0.3:1 to 1.5:1, preferably 0.7:1 to 1.2:1. In particular, glyceryl oleate citrate with the aforementioned properties improves the stability of the O/W emulsifier and emulsions based thereon.

It is also preferable for the glyceryl oleate citrate to have a pH in the range from 5 to 8, in particular 5.8 to 6.2, in particular 6.0 (measured in each case in a 10% 1:1 water/methanol blend) through neutralisation. Fully neutralised esters are particularly preferred. Sodium hydroxide, for example, is suitable for neutralisation.

The glyceryl oleate citrate in the O/W emulsifier according to the invention preferably has an HLB value in the range from 9 to 15, in particular 11 to 13.

It is also preferable for the proportion of glyceryl oleate citrate, i.e. of component (a), in the O/W emulsifier to be in the range from 75 to 85 wt. %, in particular 80 wt. %.

With the aforementioned modifications, the long-term stability of the O/W emulsifier can be significantly improved and the production of stable O/W emulsions supported.

It is also preferable for the viscosity of the viscosity modifier to be in the range from 1 to 1000 mPas, particularly preferably 1 to 100 mPas. By conforming to the specified range limits, the rheology of the O/W emulsifier can be adjusted so that it is free flowing at room temperature. This allows O/W emulsions to be cold-processed. The stated viscosity values are valid in each case for 25° C. and were determined with a Brookfield viscometer (model RV) with a suitable spindle for the particular viscosity range and at an appropriate speed of rotation for the measurement. The viscosity of the pure viscosity modifiers according to the invention was determined, wherein other suitable viscometers for measuring dynamic viscosity can be used in place of the specified viscometer, since they generally deliver only a slightly differing result.

The viscosity modifier is preferably a native oil, in particular caprylic/capric triglyceride (CAS Registry No. 65381-09-1). The latter viscosity modifier is in the form of a blend and the fatty acids contained in the triglyceride preferably have a caprylic acid content in the range from 50 to 72 wt. % and a capric acid content in the range from 26 to 45 wt. %. The choice of caprylic/capric triglyceride as the viscosity modifier in itself has a surprisingly positive effect both on the stability of the O/W emulsifier and on the emulsions prepared therewith. Caprylic/capric triglyceride is available for example from Henkel KGaA, Germany, under the trade name Myritol, or from Symrise GmbH & Co. KG, Germany, under the name Neutral Oil (2/950160).

Cosmetic and dermatological compositions in the form of an emulsion preferably contain a proportion of the O/W emulsifier according to the invention in the overall formulation in the range from 2 to 5 wt. %. If co-emulsifiers are used in compositions of the aforementioned type, their content in the overall formulation is preferably 1 to 10 wt. %. The content in the overall formulation of any stabilisers which are optionally present is preferably 0.1 to 5 wt. %.

It has also been found that glyceryl oleate citrate or the O/W emulsifier in an emulsion alone or together with other cosmetic auxiliary substances has the following effect:

Increase in the sun protection factor of UV filters (UVA and/or UVB protection); stabilising of UV filters (improved photostabilisation); improved solubility and/or suspension of solid UV filters; increase in the water resistance of sunscreen products; support for the formation of a gel network structure; increased effectiveness of active substances, such as e.g. antioxidants, preservatives, skin lighteners and tanning agents, perfume oils, chelating agents; increased substantivity of active ingredients on the skin and/or the hair; improved distribution of cosmetic oils (plant oils, mineral oils, emollients), active ingredients, vitamins, perfume oils and essential oils on the skin; support for a uniform distribution of repellent active ingredients; contribution to an optimum distribution of preservative systems in the water phase; support for the barrier function of the skin; reduction in the rate of agglomeration of inorganic UV filters (titanium dioxide, zinc oxide) and coloured pigments; support for the distribution of aluminium salts in antiperspirant products; compatibility with alcohols, also with ethanol; improved stabilisation of emulsions as the main or co-emulsifier.

Formulation examples: skin care cream (O/W), body lotion, sunscreen cream (O/W), sunscreen milk (O/W), sprayable sun milk (O/W), sensitive balsam roll-on and cream (O/W), sprayable deodorant lotion, antiperspirant lotion, hair treatment rinse, hair gel wax for men, hair cream, tinted day cream, mascara, conditioning lotion for wet wipes. Glyceryl oleate citrate or the O/W emulsifier can be formulated together with light stabilisers. Suitable light stabilisers are, for example, organic UV absorbers from the class comprising 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers (containing one or more organosilicon radicals), cinnamic acid derivatives, camphor derivatives, trianilino-s-triazine derivatives, 2-hydroxyphenylbenzotriazole derivatives, 2-phenylbenzimidazole-5-sulfonic acid and salts thereof, anthranilic acid menthyl ester, benzotriazole derivatives.

Glyceryl oleate citrate or the O/W emulsifier can also be incorporated into cosmetic and/or dermatological preparations containing pigments, preferably fine-particle pigments. They can be organic or inorganic pigments. The preferred organic pigment is 2,2'-methylene bis-[6-(2H-benzotriazol-2-yl)-4-(1,1,3,3-tetramethylbutyl)phenol] (Tinosorb® M). Inorganic pigments or micropigments based on metal oxides and/or other metal compounds which are poorly soluble or insoluble in water are in particular oxides of titanium ($TiO_2$), zinc (ZnO), iron (e.g. $Fe_2O_3$), zirconium ($ZrO_2$), silicon ($SiO_2$), manganese (e.g. MnO), aluminium ($Al_2O_3$), cerium (e.g. $Ce_2O_3$), mixed oxides of the corresponding metals and blends of such oxides. These pigments are X-ray amorphous or non-X-ray amorphous. Fine-particle pigments based on $TiO_2$ and ZnO are particularly preferred.

Glyceryl oleate citrate or the O/W emulsifier can also be incorporated into cosmetic and/or dermatological preparations which have the conventional composition and are used for cosmetic and/or dermatological light screening, also for the treatment, conditioning and cleansing of the skin and/or hair and as a makeup product in decorative cosmetics. Depending on their structure, such preparations can accordingly be used as a skin care cream, cleansing milk, sunscreen lotion, skin food, day or night cream, etc. Such preparations can thus take the form of, for example, an emulsion, lotion, milk, cream, hydrodispersion gel, balm, spray, foam, shampoo, hair care product, hair conditioner, roll-on, stick or makeup.

It is optionally possible and advantageous to use such preparations as the basis for pharmaceutical formulations. Such cosmetic and dermatological preparations are preferred in particular which are in the form of a skin care or makeup product.

For use, the cosmetic and dermatological preparations thus mentioned by way of example are applied to the skin and/or the hair in an adequate amount in the conventional way for cosmetics.

The lipid phase can advantageously be chosen from the following group of substances:

Mineral oils, mineral waxes; natural oils such as e.g. castor oil; fats, waxes and other natural and synthetic fat bodies, preferably esters of fatty acids with low C-number alcohols, for example with isopropanol, propylene glycol or glycerol, or esters of fatty alcohols with low C-number alkanoic acids or with fatty acids; alkyl benzoates; silicone oils such as dimethyl polysiloxane, diethyl polysiloxane, diphenyl polysiloxane and mixed forms thereof.

The lipid phase of the emulsions, oleogels or hydrodispersions or lipodispersions within the meaning of the present publication are advantageously chosen from the group comprising esters of saturated and/or unsaturated, branched and/or unbranched alkane carboxylic acids having a chain length of 3 to 30 C atoms and saturated and/or unsaturated, branched and/or unbranched alcohols having a chain length of 3 to 30 C atoms, from the group comprising esters of aromatic carboxylic acids and saturated and/or unsaturated, branched and/or unbranched alcohols having a chain length of 3 to 30 C atoms. Such ester oils can then advantageously be selected from the group comprising isopropyl myristate, palmitate, stearate, oleate, n-butyl stearate, n-hexyl laurate, n-decyl oleate, isooctyl stearate, isononyl stearate, isononyl isononanoate, 2-ethylhexyl palmitate, ethylhexyl laurate, 2-hexyldecyl stearate, 2-octyldodecyl palmitate, oleyl oleate, oleyl erucate, erucyl oleate and synthetic, semisynthetic and natural mixtures of such esters, e.g. jojoba oil, 2-ethylhexyl 2-ethylhexanoate, cetearyl 2-ethylhexanoate, diisopropyl adipate, triisononanoin.

The lipid phase can also advantageously be chosen from the group comprising branched and unbranched hydrocarbons and hydrocarbon waxes, silicone oils, dialkyl ethers, the group comprising saturated or unsaturated, branched or unbranched alcohols, and fatty acid triglycerides, in particular the triglycerol esters of saturated and/or unsaturated, branched and/or unbranched alkane carboxylic acids having a chain length of 8 to 24, in particular 12 to 18 C atoms. The fatty acid triglycerides can advantageously be chosen, for example, from the group comprising synthetic, semisynthetic and natural oils, e.g. olive oil, sunflower oil, soya bean oil, groundnut oil, rapeseed oil, almond oil, palm oil, coconut oil, palm kernel oil and the like.

Any blends of such oil and wax components can advantageously also be used within the context of the present invention.

Cyclomethicone (octamethyl cyclotetrasiloxane) is advantageously used within the context of the present invention as the silicone oil to be used. Other silicone oils can also be used to similar advantage, however, for example hexamethyl cyclotrisiloxane, polydimethyl siloxane, poly(methylphenyl siloxane).

Mixtures of cyclomethicone and isotridecyl isononanoate, of cyclomethicone and 2-ethylhexyl isostearate are also particularly advantageous.

The aqueous phase of preparations within the context of this invention optionally advantageously contains water-soluble plant extracts, alcohols, diols or polyols (low alkyl), and ethers thereof, preferably ethanol, isopropanol, propylene glycol, glycerol, ethylene glycol monoethyl or monobutyl ether, propylene glycol monomethyl, monoethyl or monobutyl ether, diethylene glycol monomethyl or monoethyl ether and analogous products, also alcohols (low alkyl), e.g. ethanol, 1,2-propanediol, glycerol and in particular one or more thickeners, which can advantageously be chosen from the group comprising silicon dioxide, aluminium silicates, polysaccharides or derivatives thereof, e.g. hyaluronic acid, xanthan gum, hydroxypropyl methyl cellulose, particularly advantageously from the group of polyacrylates, preferably a polyacrylate from the group of so-called carbopols, for example type 980, 981, 1382, 2984, 5984 carbopols, either individually or in combination.

The cosmetic and dermatological preparations within the context of this invention can contain cosmetic auxiliary substances, such as are conventionally used in such preparations, e.g. preservatives, antioxidants, vitamins, bactericides, perfumes, substances to prevent foaming, dyes, pigments which have a colouring effect, thickeners, surfactants, emollients, emulsifiers, wetting and/or moisture-retaining substances, moisturisers, fats, oils, waxes, plant extracts or other conventional components of a cosmetic or dermatological formulation such as alcohols, low alkyl alcohols, polyols, low alkyl polyols, polymers, foam stabilisers, complexing agents, electrolytes, organic solvents, propellant gases, silicones or silicone derivatives.

The amounts of cosmetic or dermatological auxiliary substances and carriers and perfume to be used in each case can easily be determined by the person skilled in the art, depending on the nature of the particular product.

An additional content of antioxidants is generally preferred. All antioxidants which are suitable or commonly used for cosmetic and/or dermatological applications can be used as favourable antioxidants.

The amount of antioxidants (one or more compounds) in the preparations is preferably 0.001 to 30 wt. %, particularly preferably 0.05 to 20 wt. %, in particular 1 to 10 wt. %, relative to the total weight of the preparation.

The antioxidants are advantageously chosen from the following group: amino acids (e.g. glycine, histidine, 3,4-dihydroxyphenylalanine, tyrosine, tryptophane) and derivatives thereof, imidazoles (for example urocanic acid) and derivatives thereof, peptides (D,L-carnosine, D-carnosine, L-carnosine, anserine) and derivatives thereof, carotenoids, carotenes (e.g. alpha-carotene, beta-carotene, lycopene) and derivatives thereof, chlorogenic acid and derivatives thereof, lipoic acid and derivatives thereof, aurothioglucose, propyl thiouracil and other thiols (e.g. thioredoxine, glutathione, cysteine, cystine, cystamine and glycosyl and N-acyl derivatives thereof or alkyl esters thereof) and salts thereof, dilauryl thiodipropionate, distearyl thiodipropionate, thiodipropionic acid and derivatives thereof and phenolic acid amides of phenolic benzylamines (e.g. homovanillic acid, 3,4-dihydroxyphenylacetic acid, ferulic acid, sinapic acid, caffeic acid, dihydroferulic acid, dihydrocaffeic acid, vanillomandelic acid or 3,4-dihydroxymandelic acid amides of 3,4-dihydroxybenzyl, 2,3,4-trihydroxybenzyl or 3,4,5-trihydroxybenzylamine), catechol oximes or catechol oxime ethers (e.g. 3,4-dihydroxybenzaldoxime or 3,4-dihydroxybenzaldehyde-O-ethyloxime), 2-hydrazino-1,3-thiazoles and derivatives, also (metal) chelators (e.g. 2-hydroxy fatty acids, phytic acid, lactoferrin), humic acid, bile acid, bile extracts, bilirubin, biliverdin, folic acid and derivatives thereof, ubiquinone and ubiquinol and derivatives thereof, vitamin C and derivatives thereof (e.g. ascorbyl palmitate, magnesium ascorbyl phosphate, ascorbyl acetate), tocopherols and derivatives (e.g. vitamin E acetate), vitamin A and derivatives (vitamin A palmitate), rutinic acid and derivatives thereof, flavonoids (e.g. quercetin, alpha-glycosyl rutin) and derivatives thereof, phenolic acids (e.g. gallic acid, ferulic acid) and derivatives thereof (e.g. gallic acid propyl ester, ethyl ester, octyl ester), furfurylidene glucitol, dibutyl hydroxytoluene, butyl hydroxyanisole, uric acid and derivatives thereof, mannose and derivatives thereof, zinc and derivatives thereof (e.g. ZnO, ZnSO$_4$), selenium and derivatives thereof (e.g. selenomethionine), stilbenes and derivatives thereof (e.g. stilbene oxide, resveratrol).

Likewise advantageous antioxidants are described in EP-A 900781, EP-A 1 029 849, EP-A 1 066 821, WO-A 01/43712, WO-A 01/70176, WO-A 01/98235 or in WO-A 01/98258.

If vitamin E and/or derivatives thereof are used as the antioxidant(s), it is advantageous to choose their concentrations from the range from 0.001 to 10 wt. %, relative to the total weight of the formulation.

If vitamin A or vitamin A derivatives or carotenes or derivatives thereof are used as the antioxidant(s), it is advantageous to choose their concentrations from the range from 0.001 to 10 wt. %, relative to the total weight of the formulation.

EXAMPLES

Ten formulations are provided below by way of example in which the O/W emulsifier according to the invention is called Dracorin GOC. Dracorin GOC contains 70-90 wt. % of glyceryl oleate citrate and 10-30 wt. % of caprylic/capric triglyceride. Relative to the fatty acids contained in the caprylic/capric triglyceride, the caprylic acid content is 50 to 65 wt. % and the capric acid content is 35 to 45 wt. %. The caprylic/capric triglyceride has a viscosity of approximately 30 mPas. The O/W emulsifier has a pH of approximately 6 measured in a 10% 1:1 water/methanol blend and an HLB value of approximately 12.

Example (1): cold-processable body lotion (O/W), Examples (2) and (4): sunscreen milk (O/W) and Example (3): face cream (O/W) with sunscreen;

| Name | INCI name | (1) | (2) | (3) | (4) |
|---|---|---|---|---|---|
| A Abil 100 | Dimethicone | | | 0.3 | |
| Cetiol OE | Dicaprylyl ether | | 5.0 | 1.5 | |
| Copherol 1250 | Tocopheryl acetate | | 0.5 | 0.5 | 0.5 |
| Corapan TQ ® | Diethylhexyl 2,6-naphthalate | | 5.0 | 5.0 | 2.5 |

-continued

| Name | INCI name | (1) | (2) | (3) | (4) |
|---|---|---|---|---|---|
| Cutina FS 45 | Palmitic acid (and) stearic acid | | 2.0 | | |
| Cutina MD | Glyceryl stearate | | 1.0 | 2.0 | |
| DC 345 | Cyclomethicone | 2.0 | | | |
| Dracorin GOC 2/008580 | Glyceryl oleate citrate (and) caprylic/capric triglyceride | 2.0 | 4.0 | 5.0 | 4.0 |
| Dragoxat EH 2/044115 | 2-Ethylhexyl 2-ethylhexanoate | | | 1.5 | |
| Edeta BD | Disodium EDTA | | | | 0.1 |
| Hostacerin DGMS | Polyglyceryl-2 stearate | | | | 4.0 |
| Isopropyl palmitate | Isopropyl palmitate | 7.0 | | | |
| Keltrol T | Xanthan gum | | | | 0.4 |
| Lanette 16 | Cetyl alcohol | | | 1.5 | |
| Lanette O | Cetearyl alcohol | | 1.0 | | |
| Miglyol 812 | Caprylic/capric triglyceride | | | | 5.0 |
| Neo Heliopan ® 357 | Butyl methoxydibenzoylmethane | | 0.8 | 2.0 | 1.5 |
| Neo Heliopan ® HMS | Homosalate | | | 5.0 | 8.0 |
| Neo Heliopan ® MBC | 4-Methylbenzylidene camphor | | 3.0 | | |
| Neo Heliopan ® OS | Ethylhexyl salicylate | | | 5.0 | |
| PCL Liquid 100 2/066240 | Cetearyl 2-ethylhexanoate | 8.0 | 5.0 | | |
| Prisorine 3505 | Isostearic acid | | | | 0.5 |
| SF 1214 | Cyclopentasiloxane (and) dimethicone | | | | 1.0 |
| Solbrol P | Propylparaben | | 0.1 | 0.1 | 0.1 |
| Tegosoft TN | C12–15 Alkyl benzoate | | | | 4.0 |
| Trilon BD | EDTA | | | 0.1 | |
| Zinc oxide neutral H&R | Zinc oxide | | | | 7.0 |
| B 1,3-Butylene glycol | Butylene glycol | | 3.0 | | |
| Carbopol 1382 | Carbomer | 0.2 | | | |
| Carbopol ETD 2050 | Carbomer | | 0.2 | 0.3 | |
| Glycerin 99% | Glycerin | | | 3.0 | 4.0 |
| Karion F | Sorbitol | 5.0 | | | |
| Keltrol T | Xanthan gum | | 0.2 | 0.5 | |
| Lanette E | Sodium cetearyl sulfate | | | | 0.75 |
| Sodium hydroxide solution, 10% aq. | Sodium hydroxide | 0.2 | | | 2.5 |
| Dragocid Liquid 2/060140 | Phenoxyethanol, methyl-, ethyl-, butyl-, propyl-, isobutylparaben | 0.8 | | | |
| Neo Heliopan ® AP | Disodium phenyl dibenzimidazole tetrasulfonate | | | | 2.2 |
| Neo Heliopan ® AP, 10% solution neut. with NaOH | Disodium phenyl dibenzimidazole tetrasulfonate | | 22.0 | 25.0 | |
| Phenoxyethanol | Phenoxyethanol | | 0.7 | 0.7 | 0.7 |
| Solbrol M | Methylparaben | | 0.2 | 0.2 | 0.2 |
| Water, dist. | Water (aqua) | 74.5 | 43.5 | 36.9 | 50.55 |
| C Sodium hydroxide solution, 10% aq. | Sodium hydroxide | | 2.4 | 3.5 | |
| Perfume oil | Fragrance (parfum) | | | | 0.5 |
| D Perfume oil | Fragrance (parfum) | 0.3 | 0.3 | 0.3 | |
| alpha-Bisabolol nat. | Bisabolol | | 0.1 | 0.1 | |
| (All values in %) | Total | 100 | 100 | 100 | 100 |

Example (1)

Method of Preparation (all Steps at Ambient Temperature)

Weigh out parts A/C and B separately. Mix in Carbopol using an Ultra Turrax, then neutralise. Add part B to part A/C using the Ultra Turrax and then emulsify.

Examples (2), (3)

Method of Preparation

Heat part A to approx. 85° C. For part B weigh out the raw materials without Carbopol and Keltrol. Mix in the Carbopol and Keltrol using an Ultra Turrax. Heat to approx. 85° C. Add part B to part A. Immediately add part C to A/B and then homogenise at elevated temperature (Ultra Turrax). Allow to cool whilst stirring and add part D and stir.

Example (4)

Method of Preparation

Heat part A to approx. 85° C. (without Keltrol and zinc oxide). Mix Keltrol and zinc oxide into the hot lipid phase with the Ultra Turrax. Heat part B to approx. 85° C. Add part B to part A. Cool to 60° C. whilst stirring and homogenise (Ultra Turrax). Then allow to cool to room temperature whilst stirring. Add part C and homogenise.

Example (5): hair gel wax for men DGHST 0086/01; Example (6): hair cream (O/W) DCHST 0087/00; Example (7): hair treatment rinse (O/W) with Dragoderm DLHCR 0088/00; Example (8): sensitive balsam roll-on (O/W) DRDEO 0089/00; Example (9): conditioning lotion for wet wipes (O/W) DDTSS 0091/00; Example (10): skin conditioning cream (O/W) DCSKN 0092/00

| | Raw material | INCI name | (5) | (6) | (7) | (8) | (9) | (10) |
|---|---|---|---|---|---|---|---|---|
| A | Abil 350 | Dimethicone | | | | | | 1.5 |
| | Abil B 8852 | Dimethicone copolyol | | 1.0 | | | | |
| | Cetiol HE | PEG-7 glyceryl cocoate | 1.0 | | | | | |
| | Cutina HR Plv. | Hydrogenated castor oil | | | 0.5 | | | |
| | Dracorin GMS 2/008474 | Glyceryl stearate | | | 3.0 | 2.0 | | 1.0 |
| | Drago-Oat-Active 2/060900 | Water (aqua), butylene glycol, Avena sativa (oat) kernel extr. | | | | | 1.0 | |
| | Dragoxat EH 2/044115 | Ethylhexyl ethylhexanoate | | | | | | 7.0 |
| | Dracorin GOC 2/008580 | Glyceryl oleate citrate (and) caprylic/capric triglyceride | 5.0 | | 3.0 | 3.0 | | 4.0 |
| | Eumulgin B2 | Ceteareth-20 | | | | 2.0 | | |
| | Farnesol 2/027040 | Farnesol | | 0.1 | | | | |
| | Fitoderm | Vegetable squamane | | | | | | 3.0 |
| | Lanette 16 | Cetyl alcohol | | | | | 2.5 | 4.0 |
| | Lanette O | Cetearyl alcohol | | 4.0 | 1.5 | | | |
| | Solution aid 2/014170 | PEG-40 hydrogenated castor oil, trideceth-9, water (aqua) | 15.0 | | | | | |
| | Neo-Dragocid Liquid 2/060110 | Triethylene glycol, imidazolidinyl urea, methylparaben, propylparaben, dehydroacetic acid | | | | | 0.4 | |
| | Neutral Oil 2/950161 | Caprylic/capric triglyceride | 10.0 | | | | | |
| | PCL Liquid 100 2/066240 | Cetearyl ethylhexanoate | 5.0 | 2.0 | 0.5 | 1 | | |
| | Pemulen TR-2 | Acrylates/C10–30 alkyl acrylate crosspolymer | | | | | 0.2 | |
| | Rewoderm LI 520-70 | PEG-200 hydrogenated glyceryl palmate | 1.5 | | | | | |
| | Varisoft BT 85 | Behentrimonium chloride | | | 1.0 | | | |
| | Varisoft TA 100 | Distearyldimonium chloride | | | | 2.0 | | |
| | Water | Water (Aqua) | | | | | 76.6 | |
| B | -(-alpha-)Bisabolol, nat. 2/012685 | Bisabolol | | | | | 0.1 | |
| | Aloe Vera Gel Conc. 10/1 2/912800 | Water (aqua), Aloe barbadensis gel | | | | | 1.0 | |
| | Butylene glycol | Butylene glycol | 1.0 | | | | | |
| | Citric acid, 10% in water | Citric acid | 0.3 | | | | | |
| | Dragocid Liquid 2/060140 | Phenoxyethanol, methyl-, ethyl-, butyl-, propyl-, isobutylparaben | | | 0.8 | 0.8 | | 0.8 |
| | Dragoxat EH 2/044115 | Ethylhexyl ethylhexanoate | | | | | 8.0 | |
| | Dracorin GOC | Glyceryl oleate citrate (and) caprylic/capric triglyceride | | 2.0 | | | 0.8 | |
| | Glycerin 99.5 P | Glycerin | | 6.0 | | | | 3.0 |
| | Glydant Plus Liquid | DMDM hydantoin, iodopropynyl butylcarbamate | 0.2 | | | | | |
| | Keltrol F | Xanthan gum | | | | | | 0.25 |
| | Paraffin oil 5 Gr. E | Paraffinum liquidum | | | | | 8.3 | |
| | PCL Liquid 100 2/066240 | Cetearyl ethylhexanoate | | | | | 3.9 | |
| | Water | Water (aqua) | 60.8 | 82.7 | 84.7 | 85.7 | | 75.15 |
| C | Deolite 2/027095 | Pentylene glycol, dimethyl phenylpropanol | | | | | 1.0 | |
| | Dragocid Liquid 2/060140 | Phenoxyethanol, methylparaben, ethylparaben, butylparaben, propylparaben, isobutylparaben | | 0.8 | | | | |

-continued

| Raw material | INCI name | (5) | (6) | (7) | (8) | (9) | (10) |
|---|---|---|---|---|---|---|---|
| Dragoderm 2/012550 | Glycerin, Triticum vulgare (wheat) gluten, water (aqua) | | | 3.5 | | | |
| NaOH 10% sol. | Sodium hydroxide | | | | | 0.4 | |
| Perfume oil | Fragrance | 0.2 | 0.4 | 0.5 | 1.0 | | |
| D Perfume oil | Fragrance | | | | | 0.3 | 0.3 |
| (All in %) | Total | 100 | 100 | 100 | 100 | 100 | 100 |

Example (5)

Method of Preparation

Heat phases A and B separately to approx. 75° C. Combine with moderate stirring until the gel wax is homogeneous. Then allow to cool, add phase C at approx. 40° C. and stir in until it is homogeneous. pH: approx. 5.2.

Example (6)

Method of Preparation

Mix all the raw materials from phase A, heat to 80° C. and homogenise using an Ultra Turrax. Cold-stir with a paddle agitator, reducing the stirring rate as the temperature falls. Add phase C at approx. 35° C. pH: approx. 5.9.

Examples (7) and (8)

Method of Preparation

Heat phases A and B separately to approx. 80° C. Add phase B to A (Ultra Turrax) and emulsify. Cold-stir with a paddle agitator, reducing the stirring rate as the temperature falls. Add phase C at approx. 30° C. pH: approx. 4.2 for (7) and 5.2 for (8).

Examples (9) and (10)

Method of Preparation

Swell Pemulen TR-2 or Keltrol F in water with an Ultra Turrax. Heat phases A and B separately to approx. 80° C. Add phase B to A (Ultra Turrax) and emulsify. Add phase C and homogenise again. Cold-stir with a paddle agitator, reducing the stirring rate as the temperature falls. Add phase D at approx. 35° C. pH: approx. 5.5 for (9) and 5.2 for (10).

The invention claimed is:

1. O/W emulsifier containing
   (a) 70 to 90 wt. % of glyceryl oleate citrate and
   (b) 10 to 30 wt. % of a viscosity modifier having a viscosity in the range from 1 to 10,000 mPas.
2. O/W emulsifier according to claim 1, characterised in that the glyceryl oleate citrate is an ester of monooleic and/or dioleic acid glycerides with citric acid.
3. O/W emulsifier according to claim 2, characterised in that the glyceryl oleate citrate is obtainable by esterification of citric acid with monooleic acid glyceride in a molar ratio of 0.3:1 to 1.5:1.
4. O/W emulsifier according to claim 3, characterised in that the molar ratio is in the range from 0.7:1 to 1.2:1.
5. O/W emulsifier according to claim 1, characterised in that the glyceryl oleate citrate is fully neutralised.
6. O/W emulsifier according to claim 1, characterised in that the glyceryl oleate citrate has a pH in the range from 5 to 8.
7. O/W emulsifier according to claim 6, characterised in that the pH is in the range from pH 5.8 to pH 6.2.
8. O/W emulsifier according to claim 7, characterised in that the pH is 6.0.
9. O/W emulsifier according to claim 1, characterised in that the glyceryl oleate citrate has an HLB value in the range from 9 to 15.
10. O/W emulsifier according to claim 9, characterised in that the HLB value is in the range from 11 to 13.
11. O/W emulsifier according to claim 1, characterised in that the proportion of glyceryl oleate citrate in the O/W emulsifier is in the range from 75 to 85 wt. %.
12. O/W emulsifier according to claim 11, characterised in that the proportion of glyceryl oleate citrate in the O/W emulsifier is 80 wt. %.
13. O/W emulsifier according to claim 1, characterised in that the viscosity of the viscosity modifier is in the range from 1 to 1000 mPas.
14. O/W emulsifier according to claim 13, characterised in that the viscosity of the viscosity modifier is in the range from 1 to 100 mPas.
15. O/W emulsifier according to claim 1, characterised in that the viscosity modifier is a native oil.
16. O/W emulsifier according to claim 1, characterised in that the viscosity modifier is a caprylic/capric triglyceride.
17. O/W emulsifier according to claim 16, characterised in that the caprylic acid content is 50 to 72 wt. % and the capric acid content is 26 to 45 wt. %, relative in each case to the fatty acids contained in the triglyceride.
18. A method comprising the incorporation of an O/W emulsifier according to claim 1 in cosmetic or dermatological compositions.
19. A method according to claim 18 wherein said glycerol oleate citrate in said O/W emulsifier is incorporated in a quantity sufficient for complexing metal traces in lipophilic systems, or as a solution aid for antioxidants and wherein said composition is a skin care or makeup product.
20. A method according to claim 18, characterised in that the cosmetic or dermatological composition is an emulsion and the O/W emulsifier content in the overall formulation is 2 to 5 wt. %.
21. O/W emulsion containing an O/W emulsifier according to claim 1.

* * * * *